United States Patent [19]
Fabian et al.

[11] 3,987,038
[45] Oct. 19, 1976

[54] PROCESS FOR THE PREPARATION OF 1-{[5-(4-HYDROXY-2H-1,2-BENZOTHIAZIN-3-YL)-1,2,4-OXADIAZOL-3-YL]METHYL}ETHANONE S,S-DIOXIDE

[75] Inventors: Arthur C. Fabian, Flanders; Jerome D. Genzer, Livingston; Charles Francis Kasulanis, Hopatcong; John Shavel, Jr., Mendham; Harold Zinnes, Rockaway, all of N.J.

[73] Assignee: Warner-Lambert Company, Morris Plains, N.J.

[22] Filed: May 21, 1975

[21] Appl. No.: 577,567

[52] U.S. Cl. .............................. 260/243 R
[51] Int. Cl.$^2$ .............................. C07D 279/02
[58] Field of Search .............................. 260/243 R

[56] References Cited
UNITED STATES PATENTS

| | | | |
|---|---|---|---|
| 3,787,324 | 1/1974 | Zinnes et al. | 260/243 |
| 3,822,258 | 7/1974 | Zinnes et al. | 260/243 |
| 3,868,367 | 2/1975 | Zinnes et al. | 260/243 |

*Primary Examiner*—John M. Ford
*Attorney, Agent, or Firm*—Albert H. Graddis; Frank S. Chow; Anne M. Kelly

[57] ABSTRACT

This invention relates to a process for the preparation of 1-{[5-(4-hydroxy-2H-1,2-benzothiazin-3-yl)-1,2,4-oxadiazol-3-yl]methyl} ethanone S,S-dioxide (III), a novel intermediate useful in the preparation of the known anti-inflammatory agent, 4-hydroxy-3-(5-methyl-3-isoxazolylcarbamoyl)-2-methyl-2H-1,2-benzothiazine 1,1-dioxide (IV). According to the process of this invention, the saccharin compound, 2,3-dihydro-N-(5-methyl-3-isoxazolyl)-3-oxo-1,2-benzisothiazole-2-acetamide 1,1-dioxide (I) is reacted with an alkali metal alkoxide of a lower alcohol in an inert solvent at temperatures below 30° C. to form the benzenesulfonylglycineamide, alkyl 2-{[({[(5-methyl-3-isoxazolyl)amino]carbonyl}methyl)amino]sulfonyl} benzoate (II), which is ring closed and rearranged by reaction with an alkali metal alkoxide of a lower alcohol in an inert solvent at temperatures of from 60° C. to 70° C. to form the desired oxadiazole compound III.

5 Claims, No Drawings

PROCESS FOR THE PREPARATION OF 1{[5-(4-HYDROXY-2H-1,2-BENZOTHIAZIN-3-YL)-1,2,4-OXADIAZOL-3-YL]METHYL} ETHANONE S,S-DIOXIDE

BACKGROUND OF THE INVENTION

1. Field of the Invention

The present invention relates to a process for the preparation of 1-{[5-(4-hydroxy-2H-1,2-benzothiazin-3-yl)-1,2,4-oxadiazol-3-yl]methyl ethanone} S,S-dioxide (III).

2. Description of the Prior Art

Lombardino, in U.S. Pat. No. 3,853,862 has disclosed the preparation of a series of 4-hydroxy-1,2-benzothiazine carboxamides by metal hydride ring closure of N-alkylated benzenesulfonylglycineamides. N-(5-methyl-3-isoxazolyl)-N'-methyl-N'-(2'-methoxycarbonylbenzenesulfonyl)glycineamide is among the glycineamides which may be ring closed according to the Lombardino process.

Zinnes et al. describe ring closure of the corresponding ketone (N-acetonyl-o-carbethoxybenzenesulfonamide) to form the 3-acetonylbenzothiazine, using sodium ethoxide, J. Org. Chem. 30: 2241–2246 (1965).

Rearrangement reactions of substituted isoxazoles and oxadiazoles are discussed generally in H. C. Van Der Plas, *Ring Transformations of Heterocycles*, Volume 1, Chapter 3, 1973, Academic Press, London, New York.

SUMMARY OF THE INVENTION

The saccharin derivative I:

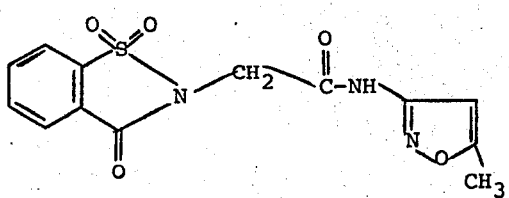

(I)

is reacted with an alkali metal alkoxide of a lower alcohol in an inert solvent at temperatures below about 30°C. to obtain the benzenesulfonylglycineamide, II:

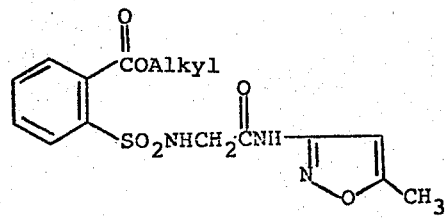

(II)

Compound II is then ring closed and rearranged in a one-step process, utilizing an alkali metal alkoxide of a lower alcohol in an inert solvent at temperatures between 60° and 70°C., to obtain the oxadiazole derivative III:

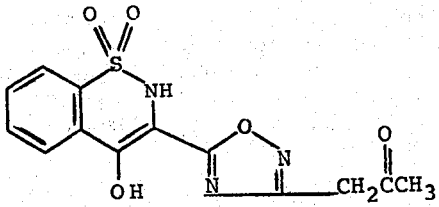

(III)

DESCRIPTION OF THE PARTICULAR EMBODIMENTS

According to the present invention, the saccharin compound I:

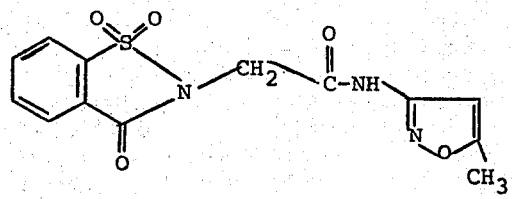

(I)

2,3-Dihydro-N-(5-methyl-3-isoxazolyl)-3-oxo-1,2-benzisothiazole-2-acetamide 1,1-dioxide is reacted with an alkali metal alkoxide of a lower alcohol (1 to 5 carbon atoms) in an inert solvent, at temperatures below about 30°C. As the solvent, a 1 to 5 carbon lower alcohol corresponding to the alcohol of the alkoxide may be used, as well as inert organic solvents such as N,N-dimethylformamide (DMF), dimethylsulfoxide (DMSO), and the like. The alkali metal alkoxide of the lower alcohol may be present in an amount of from about 2 to about 4 moles, per mole of compound I. Preferably, about 4 moles of sodium methoxide per mole of compound I in DMF, are reacted at a temperature of about 25°C. to obtain the benzenesulfonylglycineamide II:

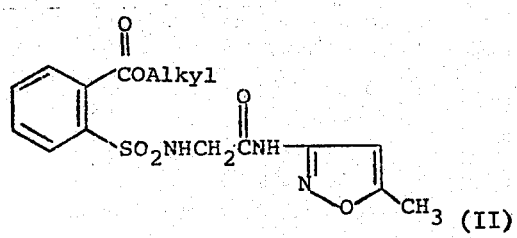

Alkyl 2-{[({[(5-methyl-3-isoxazolyl)amino]carbonyl}methyl)amino]sulfonyl}benzoate The alkyl group in compound II is determined by the particular alkoxide used in its preparation. Compound II is rearranged and ring closed in a one-step process utilizing an alkali metal alkoxide of a lower alcohol (1 to 5 carbon atoms) in an inert organic solvent, such as DMF, DMSO, or the like at temperatures of from about 60° to about 70°C., the alkali metal alkoxide of the lower alcohol being present in an amount of from about 2 to about 5 moles per mole of compound II. Preferably, about 4 moles of sodium methoxide per mole of compound II in DMF, are reacted at a temperature of about 60° to about 65°C. to obtain the desired oxidiazole III:

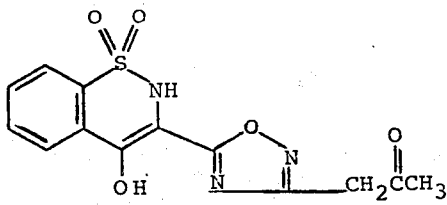

(III)

1-{[5-(4-Hydroxy-2H-1,2-benzothiazin-3-yl)-1,2,4-oxadiazol-3-yl]methyl}ethanone S,S-dioxide The starting saccharin compound I is prepared as described in co-pending U.S. application Ser. No. 577,568, filed May 21, 1975, by reacting the known compound 2-amino-5-methylisoxazole with haloacetylhalide, in, for example, chloroform containing excess pyridine. After stirring the reaction mixture for several hours, 3-(haloacetamido)-5-methylisoxazole is obtained, which is then condensed with an alkali metal salt of saccharin, such as sodium saccharin dihydrate in an inert solvent, such as dimethyformamide (100°C., 3 hours) to yield the desired saccharin compound I, the starting material of this invention.

The final product produced according to the process of this invention, 1-{[5-(4-hydroxy-2H-1,2-benzothiazin-3-yl)-1,2,4-oxadiazol-3-yl]methyl}ethanone S,S-dioxide, compound III, is a valuable intermediate in the preparation of 4-hydroxy-3-(5-methyl-3-isoxazolylcarbamoyl)-2-methyl-2H-1,2-benzothiazine 1,1-dioxide designated compound IV, which was originally described by Zinnes et al. in U.S. Pat. No. 3,822,258 as possessing anti-inflammatory properties.

Compound III of this invention may be converted into the active anti-inflammatory agent (IV) according to a novel process described in aforementioned copending U.S. application Ser. No. 577,568, filed May 21, 1975,: compound III is methylated according to conventional procedures and further treated to rearrange the oxadiazole ring to an isoxazole ring and obtain the anti-inflammatory agent, compound IV:

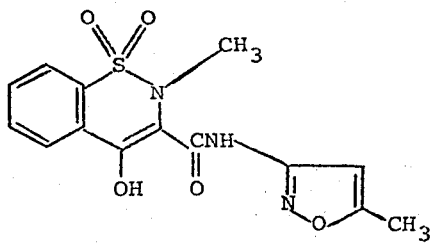

(IV)

4-hydroxy-3-(5-methyl-3-isoxazolyl)carbamoyl)-2-methyl-2H-1,2-benzo-thiazine 1,1-dioxide The aforementioned methylation reaction may be conducted in an aqueous or non-aqueous medium. In an aqueous medium, dimethylsulfate or methyliodide in an aqueous alcohol solvent system containing excess base, such as one to two equivalents of sodium hydroxide, is used. Temperature of the methylation reaction is controlled, i.e., between 10°–25°C., and upon acidification, 1-{[5-(4-hydroxy-2-methyl-2H-1,2-benzothiazin-3-yl)-1,2,4-oxadiazol-3-yl]methyl}ethanone S,S-dioxide is produced. The latter compound is rearranged to obtain the anti-inflammatory agent (IV) by heating in an inert solvent, such as xylene containing an organic base, such as triethylamine. Alternately, heating 1-{[5-(4-hydroxy-2-methyl-2H-1,2-benzothiazin-3-yl)-1,2,4-oxadiazol-3-yl]methyl}ethanone S,S-dioxide at about 90°–100°C. in an aqueous base such as sodium hydroxide also affords IV, after acidification.

Alternatively, compound III may be converted to compound IV using conventional methylating agents in aqueous alcohols containing an excess of base at elevated temperatures. For example, compound III is placed in SOLOX containing an excess, preferably 3.5 equivalents of aqueous sodium hydroxide, with an excess, preferably 1.5 equivalents of dimethylsulfate, and heated at reflux (about 75°C. to 80°C.) for about 1½ hours. After acidification, compound IV is obtained.

Direct conversion of compound III to compound IV is also effected in a non-aqueous medium, such as dimethylformamide, at elevated temperatures (about 50° to 80°C., preferably 60°C.), using an excess, preferably two equivalents of a metal hydride base, preferably sodium hydride, followed by the addition of a conventional methylating agent, such as methyl iodide. Acidification affords compound IV.

The corresponding alkali metal, alkaline earth metal and amine salts of final compound IV may be prepared by treating compound IV with the desired base, e.g., sodium alkoxide, potassium alkoxide, sodium hydroxide, potassium hydroxide, calcium hydroxide, pyrrolidine and the like according to conventional procedures. If desired, the alkali metal salt of compound IV may be obtained directly in certain of the above-described procedures by omission of the acidification reaction in the final process step.

The known 2-amino-5-methylisoxazole is commercially available from Hoffmann La Roche, Nutley, N.J., and may be prepared as described in Netherlands Pat. No. 6,511,924.

The anti-inflammatory agent IV, 4-hydroxy-3-(5-methyl-3-isoxazolylcarbamoyl)-2-methyl-2H-1,2-benzothiazine 1,1-dioxide is described in U.S. Pat. No. 3,816,628, as useful as an anti-inflammatory, antipyretic or analgesic agent. When administered orally to rats at a dose of 10–200 mg/kg, it is able to cause reduction in swelling of the paw induced by injection into the foot pads of an irritant such as carrageenin. Therapeutically or propylactically administered orally at a dose of 15–200 mg/kg, compound IV inhibits adjuvant induced polyarthritis in the rat. Oral doses of 25–100 mg/kg are sufficient to inhibit yeast induced hyperthermia in the rat. At oral doses of 25–200 mg/kg it exhibits a significant analgesic effect as determined by the phenylquinone writhing procedure in mice.

Generally speaking, the anti-inflammatory agent IV is indicated in conditions such as pain resulting from arthritis, bursitis, and the like. A daily dosage regimen of about 0.5 grams to about 2 grams in several divided doses is recommended for a mammal weight about 70 kg body weight to relieve the pain and swelling associated with these conditions. Compound IV may be administered either orally or by injection.

In order to use compound IV, it is formulated into dosage forms such as tablets or syrups by blending with an inert pharmaceutical carrier such as lactose or simple syrup by methods well known to the pharmacists art. For injectionable dosage forms, it is formulated with vehicles such as water, peanut oil, sesame oil, and the like. In these dosage forms, the active ingredient is from about 0.5 grams to 1 gram per dosage unit.

The following definitions apply to all of the compounds and reaction procedures of this invention, as well as to reagents and intermediates used in the preparation thereof: halogen is meant to include chlorine, bromine and iodine; the term alkali metal is meant to include sodium, potassium and the like; the term lower alcohol is meant to include 1 to 5 carbon, straight or branched chain alcohols; the term base is meant to include those bases commonly used in an aqueous reaction medium, such as sodium hydroxide, potassium hydroxide and the like; the term organic base is meant to include those bases commonly used in a non-aqueous reaction medium, such as pyridine, diethylamine, triethylamine, and the like; the term metal hydride base is meant to include alkali metal and alkaline earth metal hydrides such as sodium hydride, potassium hydride, calcium hydride and the like.

In order to further illustrate this invention, the following examples are provided:

EXAMPLE 1

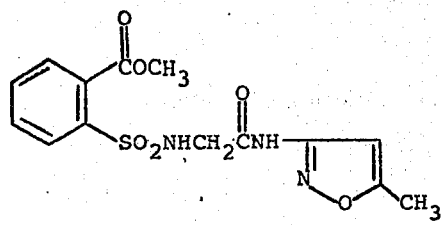

Methyl 2-{[({[(5-Methyl-3-Isoxazolyl)Amino]Carbonyl}Methyl)Amino]Sulfonyl}Benzoate To 60 ml DMF is added 13.5 grams (0.25 mole) of sodium methoxide. To this slurry at 15°C. is added a solution of 20 grams (0.062 mole) of 2,3-dihydro-N-(5-methyl-3-isoxazolyl)-3-oxo-1,2-benzisothiazole-2-acetamide 1,1-dioxide dissolved in 70 ml DMF. The reaction mixture is stirred at 25°-30°C. for a half hour whereupon it is acidified and extracted with chloroform. These extracts are washed with sodium bicarbonate and water, dried (na₂SO₄) and concentrated to an oil which is triturated with petroleum ether to give 16.3 grams (75%) of methyl 2-{[({[(5-methyl-3-isoxazolyl-)amino]carbonyl}methyl)amino]sulfonyl}benzoate, mp 153°-156°C.

Analysis: Calc'd for $C_{14}H_{15}N_3O_6S$. C, 47.59; H, 4.28; N, 11.89; S, 9.07. Found: C, 47.53; H, 4.21; N, 11,78; S, 9.18.

EXAMPLE 2

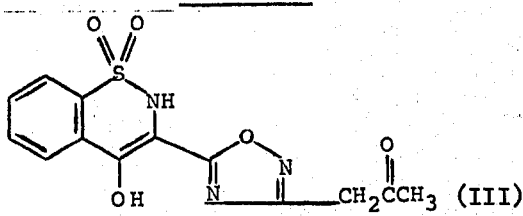

1-{[5-(4-Hydroxy-2H-1,2-Benzothiazin-3-yl)-1,2,4-Oxadiazol-3-yl]Methyl Ethanone}S,S-Dioxide (III)

To 24 ml of DMF is added 4.89 grams (0.09 mole) of NaOMe. This is heated to 55°C. whereupon a solution of 8 grams (0.023 mole) of methyl 2-{[({[(5-methyl-3-isoxazolyl)amino]carbonyl}methyl)amino]sulfonyl}-benzoate dissolved in 28 ml of DMF is added. A temperature of 60°-65°C. is maintained for 30 minutes whereupon the reaction mixture is cooled and acidified. This afforded 4.8 grams (65%) of crude product III. Purification (MeOH/H₂O) afforded 1-{[5-(4-hydroxy-2H-1,2-benzothiazin-3-yl)-1,2,4-oxadiazol-3-yl]methyl}ethanone S,S-dioxide, mp 186-187°C. which was identical, in all aspects, to the compound disclosed and designated as "compound V" in co-pending U.S. application Ser. No. 577,568 filed May 21, 1975.

We claim:

1. A process for the preparation of a compound having the formula III which comprises the following steps:

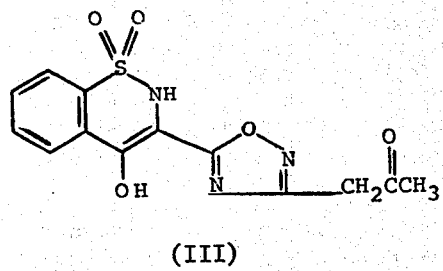

(III)

A. reacting a compound having the formula I:

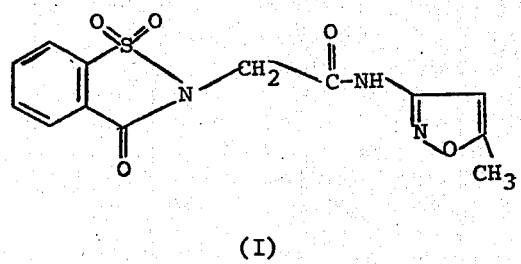

(I)

with an alkali metal alkoxide of a lower alcohol in an inert solvent at temperatures below about 30°C. to obtain a compound of the formula II:

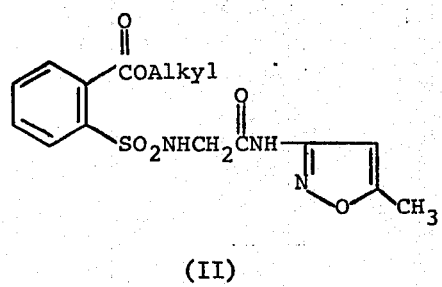

(II)

B. reacting compound II with an alkali metal alkoxide of a lower alcohol in an inert solvent at temperatures between about 60°C. and about 70°C. to obtain the desired compound III.

2. A process according to claim 1 wherein, in Step A, the solvent is selected from the group consisting of 1 to 5 carbon lower alcohols, dimethylsulfoxide and dimethylformamide.

3. A process according to claim 2 wherein, in Step A, the reaction is conducted in dimethylformamide using sodium methoxide, at a temperature of about 25°C.

4. A process according to claim 1 wherein, in Step B, the solvent is selected from the group consisting of dimethylsulfoxide and dimethylformamide.

5. A process according to claim 4 wherein, in Step B, the reaction is conducted in dimethylformamide using sodium methoxide and a temperature of from about 60°C. to about 65°C.

* * * * *